(12) United States Patent
Koizumi

(10) Patent No.: US 12,011,142 B2
(45) Date of Patent: Jun. 18, 2024

(54) ELECTRONIC ENDOSCOPE SYSTEM

(71) Applicant: HOYA CORPORATION, Tokyo (JP)

(72) Inventor: Ryohey Koizumi, Tokyo (JP)

(73) Assignee: HOYA CORPORATION, Tokyo (JP)

(*) Notice: Subject to any disclaimer, the term of this patent is extended or adjusted under 35 U.S.C. 154(b) by 675 days.

(21) Appl. No.: 17/283,816

(22) PCT Filed: Mar. 26, 2020

(86) PCT No.: PCT/JP2020/013862
§ 371 (c)(1),
(2) Date: Apr. 8, 2021

(87) PCT Pub. No.: WO2020/203705
PCT Pub. Date: Oct. 8, 2020

(65) Prior Publication Data
US 2021/0338039 A1 Nov. 4, 2021

(30) Foreign Application Priority Data
Apr. 2, 2019 (JP) ................. 2019-070601

(51) Int. Cl.
A61B 1/00 (2006.01)
G06T 7/00 (2017.01)

(52) U.S. Cl.
CPC .... A61B 1/000094 (2022.02); A61B 1/00004 (2013.01); A61B 1/0005 (2013.01);
(Continued)

(58) Field of Classification Search
CPC .......... A61B 1/000094; A61B 1/00004; A61B 1/0005; G06T 2207/10068; G06T 2207/20021; G06T 2207/30096
(Continued)

(56) References Cited

U.S. PATENT DOCUMENTS

2015/0187063 A1 7/2015 Takahashi
2015/0313445 A1 11/2015 Davidson et al.
(Continued)

FOREIGN PATENT DOCUMENTS

JP 2012-228346 11/2012
WO 2014/192512 12/2014
(Continued)

OTHER PUBLICATIONS

Official Communication issued in International Bureau of WIPO Patent Application No. PCT/JP2020/013862, dated Jun. 23, 2020.

Primary Examiner — John W Miller
Assistant Examiner — Omer Khalid
(74) Attorney, Agent, or Firm — GREENBLUM & BERNSTEIN, P.L.C.

(57) ABSTRACT

This electronic endoscope system includes an evaluation unit that evaluates an extent of a lesion by processing an image inside an organ image-captured by an electronic endoscope. The evaluation unit includes: an image evaluation value calculation unit that calculates an image evaluation value for the captured image; a lesion evaluation unit that calculates a representative evaluation value of image evaluation values from the image evaluation value for each of a plurality of spaces to evaluate the spread of the lesion; and a lesion evaluation adjustment unit that sets, for an empty section for which a representative evaluation value is not generated, as an estimated representative evaluation value, one image evaluation value for a non-empty section, or a representative evaluation value obtained on the basis of the image evaluation value, and that assigns the estimated representative evaluation value to the empty section.

7 Claims, 7 Drawing Sheets

(52) U.S. Cl.
CPC .. *G06T 7/0012* (2013.01); *G06T 2207/10068* (2013.01); *G06T 2207/20021* (2013.01); *G06T 2207/30096* (2013.01)

(58) Field of Classification Search
USPC .......................................................... 348/65
See application file for complete search history.

(56) References Cited

U.S. PATENT DOCUMENTS

| | | |
|---|---|---|
| 2018/0279866 A1 | 10/2018 | Makino |
| 2019/0192048 A1 | 6/2019 | Makino et al. |

FOREIGN PATENT DOCUMENTS

| | | | | |
|---|---|---|---|---|
| WO | 2017/057680 | 4/2017 | | |
| WO | 2018/043550 | 3/2018 | | |
| WO | WO-2018043550 A1 * | 3/2018 | ......... | A61B 1/00009 |

* cited by examiner

ELECTRONIC ENDOSCOPE SYSTEM

TECHNICAL FIELD

The present invention relates to an electronic endoscope system and a data processing device for evaluating a spread of a lesion of biological tissue inside an organ.

BACKGROUND ART

Lesion parts in biological tissue have varying levels of severity, from inflammation in which a mucosal layer of the biological tissue becomes thin, rough, and red, to ulcers that are partially missing from the mucosal layer and a lower layer thereof. For example, an ulcer part of a lesion of an ulcerative colitis (UC) is white with white moss and purulent mucus, and an inflammation part is reddish with edema and easy bleeding. Such a lesion part can be captured and observed by an endoscope system.

However, in order for a surgeon to be able to distinguish between a normal part and the lesion part by the difference in color included in the endoscopic image, it is necessary to undergo long-term training under the guidance of an expert. Moreover, it is not easy for an experienced surgeon to identify the lesion part with a slight color difference, so careful work is required. Therefore, it is preferable that the endoscope system provides an evaluation result in which an extent of a lesion in the lesion part is objectively quantified.

On the other hand, an endoscope system that can suppress fluctuations in an evaluation value of an inflammation part to perform a stable calculation of the evaluation value and suppress a processing load of the calculation of the evaluation value has been known (Patent Literature 1).

CITATION LIST

Patent Literature

Patent Literature 1: WO 2017/057680 A

SUMMARY OF INVENTION

Technical Problem

The above-described endoscope system includes a light source device that irradiates illumination light toward a subject, an image acquisition unit that is obtained by capturing an image of reflected light from the subject with an image sensor and acquires a color image including at least three or more color components, and an evaluation unit that obtains evaluation results for target diseases of each pixel based on an angle formed by a line segment connecting a predetermined reference point set in a color plane and pixel corresponding points in the color plane of each pixel constituting the color image acquired by the image acquisition unit and a reference axis with a correlation to the target disease, within the color plane defined by at least two of at least three color components. The reference axis is set so as to pass through a predetermined reference point. The reference axis is at least one of an axis having a correlation with a target disease whose degree of inflammation is equal to or less than a predetermined value and an axis having a correlation with a target disease whose degree of inflammation is equal to or greater than a predetermined value in the color plane.

According to such a configuration, it is possible to suppress the fluctuations in the inflammation evaluation value due to the brightness of the image, perform the stable calculation of the inflammation evaluation value, and suppress the processing load of the calculation of the inflammation evaluation value.

However, when the endoscope system evaluates an extent of a lesion such as inflammation of biological tissue inside the organ, the evaluation is limited to a part of biological tissue whose image is captured, and it is possible to appropriately perform how much a site with some degree of inflammation is spread in the depth direction in the organ. By assessing the spread of the inflammation part in the depth direction, a method of treating a lesion part may be often different.

Furthermore, it is important to divide the inside of the organ into a plurality of sections in which the organ is characterized and to know the extent of the lesions for each section in order to evaluate the spread of the lesion in the depth direction, but the extent of the lesions are not evaluated in all the sections, and there are some empty sections in which the extent of the lesions are not evaluated. In such a case, even if the condition of the progress of the lesions for each section may be evaluated by examining the same organ at a later date, if the previous evaluation result has the empty section without the evaluation result of the extent of the lesion, it is difficult to grasp the condition of the progress (or a condition of a reduction) of the lesion in the depth direction.

Therefore, an object of the present invention is to provide an electronic endoscope system and a data processing device capable of a spread of a lesion in a depth direction of an organ even if there is an empty section without an evaluation result of an extent of a lesion in a plurality of sections obtained by dividing a region inside the organ when the extent of the lesion such as the inflammation of biological tissue in the organ is evaluated.

Solution to Problem

One aspect of the present invention is an electronic endoscope system that evaluates an extent of a lesion in biological tissue in an organ from an image of the biological tissue that an electronic endoscope inserted into the organ captures. The electronic endoscope system includes:
an electronic endoscope configured to capture the image of the biological tissue in the organ; and
a processor including an evaluation unit configured to process a plurality of captured images of the biological tissue to evaluate the extent of the lesion in the organ; and
a monitor configured to display an evaluation result of the extent of the lesion on a screen.
The evaluation unit includes:
an image evaluation value calculation unit configured to calculate an image evaluation value indicating the extent of the lesion in an image of interest for at least some of a plurality of images of interest of a plurality of images that are obtained by capturing different locations of the biological tissue in the organ;
an image-captured position information processing unit configured to associate the information on the image-captured position in the organ captured by the electronic endoscope with each of the images of interest;
a lesion evaluation unit configured to sort each of the calculated image evaluation values to one of a plurality of sections obtained by dividing the region inside the organ by using the information on the image-captured position, perform processing to generate a representative evaluation values for each section from the sorted image evaluation value, and evaluate the spread of the lesion continuously spreading in the depth direction of the organ using the representative evaluation value; and a lesion evaluation adjustment unit configured to assign one of the image evaluation values in a non-empty section which is located on a back side of the organ from an empty section and has the representative evaluation value generated therein among the plurality of sections, or a representative evaluation value obtained based on the image evaluation value in the non-empty section to the empty section as an estimated representative evaluation value in the empty section, for the empty section in which the representative evaluation value is not generated by the processing of the lesion evaluation unit among the plurality of sections.

The lesion evaluation adjustment unit may define one of the image evaluation values in a section nearest to the empty section or the representative evaluation value in the nearest section as the estimated representative evaluation value, in the non-empty section on the back side of the organ from the empty section.

The image or the image evaluation value may be associated with information on a capture time or a capture order of the image, and the lesion evaluation adjustment unit may define an image evaluation value corresponding to an image at which the capture time or the capture order is the latest among the images that capture the non-empty section on the back side of the organ from the empty section or the image evaluation value of the image at which the capture time or the capture order is the latest among the image evaluation values of the images that capture the non-empty section on the back side of the organ from the empty section, as the estimated representative evaluation value.

Another aspect of the present invention is an electronic endoscope system that evaluates an extent of a lesion in biological tissue in an organ from an image of the biological tissue that an electronic endoscope inserted into the organ captures. The electronic endoscope system includes:

an electronic endoscope configured to capture the image of the biological tissue in the organ; and a processor including an evaluation unit configured to process a plurality of captured images of the biological tissue to evaluate the extent of the lesion in the organ; and a monitor configured to display an evaluation result of the extent of the lesion on a screen.

The evaluation unit includes:

an image evaluation value calculation unit configured to calculate an image evaluation value indicating the extent of the lesion in an image of interest for at least some of a plurality of images of interest of a plurality of images that are obtained by capturing different locations of the biological tissue in the organ;

an image-captured position information processing unit configured to associate the information on the image-captured position in the organ captured by the electronic endoscope with each of the images of interest;

a lesion evaluation unit configured to sort each of the calculated image evaluation values to one of a plurality of sections obtained by dividing the region inside the organ by using the information on the image-captured position, perform processing to generate representative evaluation values for each section from the sorted image evaluation value, and evaluate the spread of the lesion continuously spreading in the depth direction of the organ using the representative evaluation value; and a lesion evaluation adjustment unit configured to set two of the representative evaluation values in each non-empty section which has an empty section sandwiched between both sides thereof among the plurality of sections and has the representative evaluation value generated therein as a reference evaluation value, and assign a composite evaluation value calculated based on the reference evaluation value to the empty section as an estimated representative evaluation value in the empty section, for the empty section in which the representative evaluation values are not generated by the processing of the lesion evaluation unit among the plurality of sections.

The lesion evaluation adjustment unit may define, as the estimated representative evaluation value, a weighted average value obtained by weighting and averaging the two reference evaluation values using a first weighting coefficient based on total length information of length information of one of the non-empty sections on both the sides and length information of the empty section and a second weighting coefficient based on total length information of length information of the other of the non-empty sections on both the sides and the length information of the empty section.

Still another aspect of the present invention is an electronic endoscope system that evaluates an extent of a lesion in biological tissue in an organ from an image of the biological tissue that an electronic endoscope inserted into the organ captures. The electronic endoscope system includes:

an electronic endoscope configured to capture the image of the biological tissue in the organ; and a processor including an evaluation unit configured to process a plurality of captured images of the biological tissue to evaluate the extent of the lesion in the organ; and a monitor configured to display an evaluation result of the extent of the lesion on a screen.

The evaluation unit includes:

an image evaluation value calculation unit configured to calculate an image evaluation value indicating the extent of the lesion in an image of interest for at least some of a plurality of images of interest of a plurality of images that are obtained by image-capturing different locations of the biological tissue in the organ;

an image-captured position information processing unit configured to associate the information on the image-captured position obtained by dividing the organ captured by the electronic endoscope with each of the images of interest;

a lesion evaluation unit configured to sort each of the calculated image evaluation values to one of a plurality of sections obtained by dividing the region inside the organ by using the information on the image-captured position, perform processing to generate a representative evaluation values for each section from the sorted image evaluation value, and evaluate the spread of the lesion continuously spreading in the depth direction of the organ using the representative evaluation value; and a lesion evaluation adjustment unit configured to assign a composite representative evaluation value obtained based on the representative evaluation values in each non-empty section which has an empty section sandwiched between both sides thereof and has the representative evaluation values generated therein among the plurality of sections, for the empty section in which the representative evaluation values are not generated by the processing of the lesion evaluation unit among the plurality of sections to the empty section as an estimated representative evaluation value indicating the extent of the lesion in the empty section, and the lesion evaluation adjustment unit calculates the estimated representative evaluation value in the empty section by interpolation by curve fitting using length information of each of the non-empty sections on both sides, length information of the empty section, and the representative evaluation values in the non-empty section and the empty section.

The evaluation unit may include an evaluation result integration unit configured to generate an evaluation result screen displaying the representative evaluation value and the estimated representative evaluation value corresponding to the section, and in the evaluation result screen, the estimated representative evaluation value may be represented in a display form that can be distinguished from the representative evaluation value.

Further, the electronic endoscope system may further include a lesion part position calculation unit configured to set, as a start position or an end position of a lesion part, a position where the image evaluation value of the image of interest crosses a preset threshold value with the movement of the image-captured position of the image of interest and specify the start position or the end position in the organ from the information on the image-captured position of the image of interest, in which the lesion evaluation unit may calculate the length in the depth direction of the lesion part from a specific result of the lesion part position calculation unit.

Another aspect of the present invention is a data processing device that evaluates an extent of a lesion in biological tissue in an organ from an image of the biological tissue that an electronic endoscope inserted into the organ captures, the data processing device including: an image evaluation value calculation unit configured to calculate an image evaluation value indicating the extent of the lesion in an image of interest for at least some of a plurality of images of interest of a plurality of images that are obtained by image-capturing different locations of the biological tissue in the organ;

an image-captured position information processing unit configured to associate the information on the image-captured position in the captured organ with each of the images of interest;

a lesion evaluation unit configured to sort each of the calculated image evaluation values to one of a plurality of sections obtained by dividing the region inside the organ by using the information on the image-captured position, perform processing to generate a representative evaluation values for each section from the sorted image evaluation value, and evaluate the spread of the lesion continuously spreading in the depth direction of the organ using the representative evaluation value; and a lesion evaluation adjustment unit configured to assign, to the empty section as an estimated representative evaluation value in the empty section, one of the image evaluation values in a non-empty section which is located on a back side of the organ and in which the representative evaluation value is generated by an evaluation unit, among the plurality of sections, for the empty section in which the representative evaluation value is not generated by the processing of the lesion evaluation unit, or a representative evaluation value obtained based on the image evaluation value in the non-empty section among the plurality of sections.

Further, the electronic endoscope system may further include a lesion part position calculation unit configured to set, as a start position or an end position of a lesion part, a position where the image evaluation value of the image of interest crosses a preset threshold value with the movement of the image-captured position of the image of interest and specify the start position or the end position in the organ from the information on the image-captured position of the image of interest, in which the lesion evaluation unit may calculate the length in the depth direction of the lesion part from a specific result of the lesion part position calculation unit.

Advantageous Effects of Invention

According to the electronic endoscope system and the data processing device described above, when evaluating the extent of the lesion of biological tissue inside the organ, even if there is the empty section without the evaluation result of the extent of the lesion, it is possible to evaluate the spread of biological tissue in the depth direction of the organ.

DESCRIPTION OF EMBODIMENTS

Figure 1:
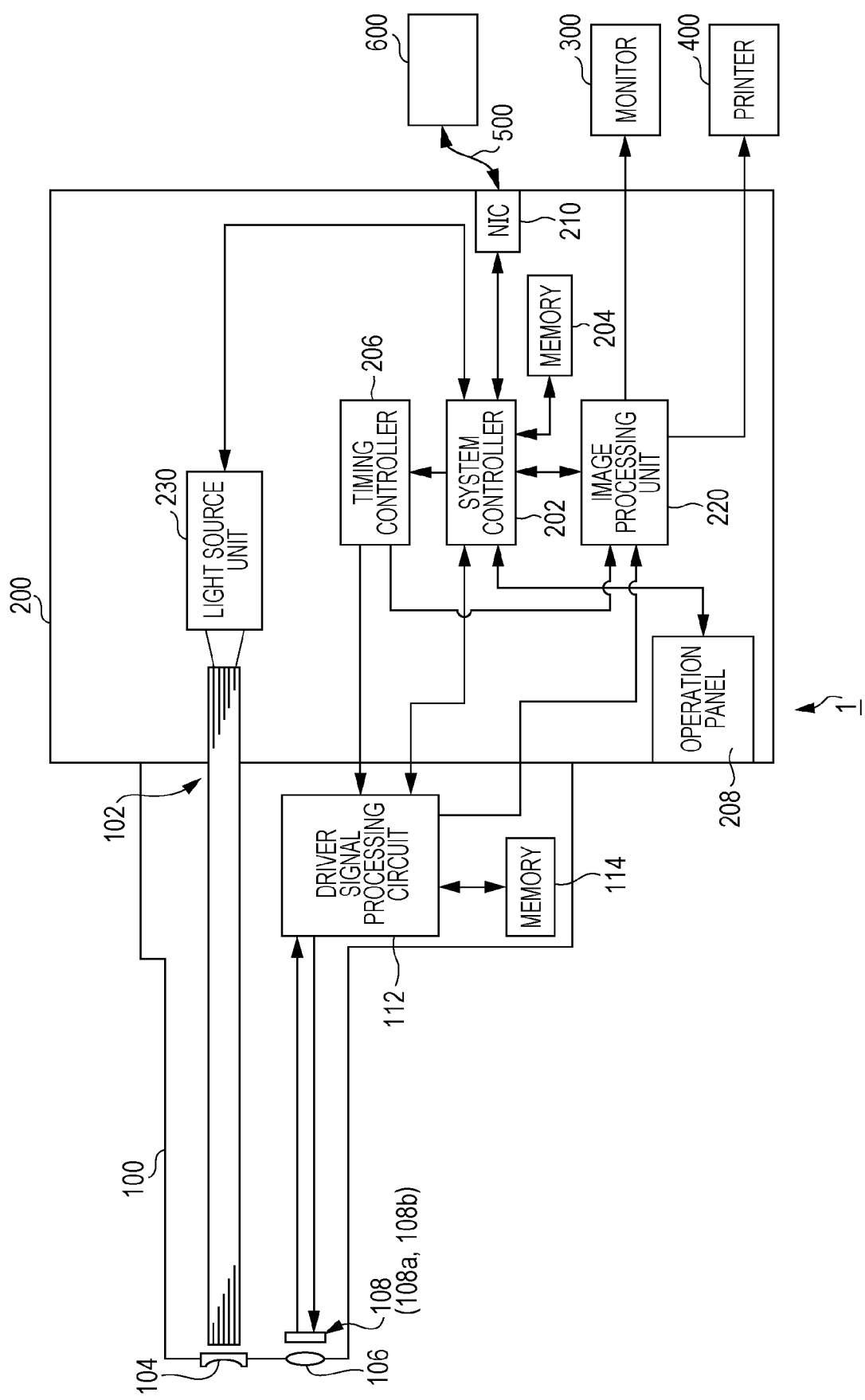
FIG. 1 is a block diagram illustrating a configuration of an endoscope system according to an embodiment.

Hereinafter, before explaining an electronic endoscope system and a data processing device of an embodiment of the present invention with reference to the drawings, first, an evaluation of a spread of a lesion inside an organ will be conceptually described.

(Summary of Evaluation of Extent of Lesion Inside Organ)

A processor of the electronic endoscope system according to an embodiment of the present invention evaluates an extent of a lesion in biological tissue in an organ from an image of the biological tissue that an electronic endoscope inserted into the organ captures. The extent of the lesion includes the spread and strength of the lesion. When capturing an image of the biological tissue inside the organ, for example, the electronic endoscope is inserted from an opening end of a tubular organ to a position of a deepest portion to be captured in a depth direction inside the organ, and captures an image of the biological tissue inside the organ while continuously moving from the position toward the opening end of the organ. The depth direction includes both a direction from the opening end to the deepest portion and a direction from the deepest portion to the opening end.

The captured image of the biological tissue may be a moving image continuously captured at regular time intervals, or may be a still image captured intermittently while moving the electronic endoscope in the organ. When moving the electronic endoscope, the moving speed of the electronic endoscope does not necessarily have to be constant, and the electronic endoscope can return to the location where the electronic endoscope has passed and captures the image, that is, the moving direction thereof can also be partially reversed. Note that in the case of the moving image, the electronic endoscope performs capturing while moving in substantially the same direction at substantially the same moving speed.

In the evaluation of the extent of the lesion, the processor calculates image evaluation values indicating the strength of the lesion in the image instructed by a surgeon or an operator, for each of the plurality of images of biological tissue illuminated with white illumination light. The image evaluation value is not particularly limited, but when the lesion is inflammation, examples thereof can include a inflammation value obtained by evaluating a degree of inflammation of a lesion part (inflammation part) based on information on a color component of the lesion part (for example, red).

The organ to be evaluated is not particularly limited, and examples thereof can include a digestive tract such as pharynx to esophagus, stomach, a small intestine, and a large intestine.

Further, for example, the biological tissue is illuminated with special light including fluorescence of 445 to 700 nm in which a phosphor is emitted with a laser beam having a wavelength of 405 nm, a laser beam having a wavelength of 445 nm, and a laser beam having a wavelength of 445 nm, and captured, a ratio of two image signals from three RGB image signals obtained by the capture is created, and evaluation values for each image created by using a processing result of performing predetermined enhancement processing on these two image signals, for example, evaluation values for evaluating a mucous membrane or the like in atrophic gastritis can also be used as the image evaluation values.

Further, for example, the biological tissue is illuminated and captured by using light having a wavelength of 600 nm, light having a wavelength of 630 nm, and light having a wavelength of 540 nm as illumination light, and the evaluation values for each image created by using the processing result of performing the predetermined enhancement processing on the image obtained by the capturing, for example, the evaluation values for evaluating a condition of blood vessels in a deep portion of the mucous membrane can also be used as the image evaluation values.

In addition, cells in a mucous membrane of a digestive tract, which are illuminated with light and are pretreated by staining, are enlarged and captured, and such as an average value of a feature quantity (shape information such as a length, a diameter, a perimeter, and roundness) of a cell nucleus, an evaluation value for evaluating an extent of a lesion such as non-tumor, adenoma, and cancer, and the like can also be used as the image evaluation value.

Further, the image evaluation value may be an evaluation value such as a Mayo score obtained for each image. In this case, the evaluation value calculated by using the evaluation device machine-learned from the captured image may be used as the above image evaluation value. Further, the image evaluation value may be a value obtained by quantifying a histopathological evaluation for each image.

In this case, when each image is captured, the acquired information on the image-captured position inside the captured organ is associated with each image.

The processor uses the acquired information on the image-captured position to calculate the representative evaluation value of the image evaluation value from the image evaluation values of a plurality of images of biological tissue captured within the plurality of sections, respectively, for each of the plurality of sections obtained by dividing the region of the captured organ, and uses the representative evaluation value to evaluate the spread of the lesion which is continuously spreading in the depth direction of the organ.

Here, the section is a section divided by a distance equal to or greater than a sampling interval of the image-captured position. According to an embodiment, this section is a section divided at a predetermined interval. The predetermined interval may be a constant interval or may not be constant. Further, the predetermined interval may change at any time during the calculation of the representative evaluation value. For example, sections divided at fine intervals in advance may change to a larger section, for example, a segment which is a part that can be identifiably distinguished from other parts in an organ.

According to an embodiment, the evaluation of the extent of the lesion includes obtaining the representative values of the image evaluation values corresponding to each of the plurality of sections, displaying a distribution of the representative evaluation value in the depth direction, or providing a total value of the representative evaluation values corresponding to the sections including the lesion part that is assessed using the image evaluation values. As a result, the extent of the lesion in which the spread and strength of lesion are evaluated at the same time can be divided and evaluated by a level.

The representative evaluation value is a statistic of the image evaluation values for each section, for example, the average value, the median value, the most frequent value, or the maximum value. Further, when calculating the representative evaluation value while playing back the image, the image evaluation value calculated at the end of each section may be used as the representative evaluation value.

In this way, the representative evaluation values of the image evaluation values are calculated from the image evaluation values obtained from the images for each of the plurality of sections obtained by dividing the region inside the captured organ using the information on the image-captured position inside the captured organ, so the spread of the lesion can be evaluated accurately. However, such an image evaluation value is an evaluation value for an image instructed by a surgeon or an operator, and does not always exist for each section. When the surgeon or operator determines that the extent of the lesion is assessed not to be changed while looking at the image displayed on the monitor after capturing, the instruction is not frequently input as the image to be calculated for the image evaluation value. In this case, there is an empty section without representative evaluation value. Therefore, even if an attempt is made to compare the degree of spread of the lesion by referring to the evaluation result with an empty section at a later date, the spread of the lesion may not be evaluated accurately because there is the empty section.

Therefore, in the electronic endoscope system of the present embodiment, the processor is provided with a lesion evaluation adjustment unit. For the empty section in which the representative evaluation value is not generated, the lesion evaluation adjustment unit is configured to assign one of the image evaluation values in a non-empty section which is located on a back side of an organ from an empty section and has the representative evaluation value generated therein or the representative evaluation value obtained based on the image evaluation value in the non-empty section to an empty section as the estimated representative evaluation value in the empty section.

Alternatively, for the empty section in which the representative evaluation values are not generated, the lesion evaluation adjustment unit is configured to set two of representative evaluation values in each non-empty section which has an empty section sandwiched between both sides thereof among a plurality of sections as a reference evaluation value, and assign a composite evaluation value calculated based on the reference evaluation value to the empty section as an estimated representative evaluation value indicating the extent of the lesion in the empty section.

Alternatively, for the empty section in which the representative evaluation values are not generated, the lesion evaluation adjustment unit is configured to assign a composite representative evaluation value obtained based on a representative evaluation value in a non-empty section which has an empty section sandwiched between both sides thereof among the plurality of sections to the empty section as an estimated representative evaluation value indicating the extent of the lesion in the empty section. In this case, the lesion evaluation adjustment unit calculates the estimated representative evaluation value in the empty section by the interpolation by the curve fitting using the length information of each of the non-empty sections on both sides, the length information of the empty section, and the representative evaluation values in the non-empty section.

Note that the representative evaluation value and the estimated representative evaluation value are an indicator of the strength of lesion in the section. Therefore, it is possible to accurately evaluate not only the strength of lesion of the local biological tissue for each of the plurality of captured images, but also the comprehensive evaluation including the spread and strength of lesion in the depth direction of the organ. Here, the spread of the lesion indicates that the lesions are continuously spreading in the depth direction. Therefore, it is difficult to evaluate the spread of the lesion even if the image evaluation value is calculated by discretely capturing the images at several positions in the organ.
(Description of Electronic Endoscope System)

FIG. 1 is a block diagram illustrating a configuration of an electronic endoscope system 1 according to an embodiment of the present invention.

As illustrated in FIG. 1, the electronic endoscope system 1 includes an electronic scope (electronic endoscope) 100, a processor 200 for an electronic endoscope, a monitor 300, and a printer 400.

The processor 200 for an electronic endoscope includes a system controller 202 or a timing controller 206. The system controller 202 executes various programs stored in a memory 204 and controls the entire of the electronic endoscope system 1 in an integrated manner. Further, the system controller 202 changes various settings of the electronic endoscope system 1 according to an instruction of a surgeon or an operator input from the operation panel 208. The timing controller 206 outputs a clock pulse for adjusting an operation timing of each part to each circuit in the electronic endoscope system 1.

The processor 200 for an electronic endoscope includes a light source unit 230 that supplies illumination light to the electronic scope 100. Although not illustrated, the light source unit 230 includes, for example, a high-intensity lamp, which emits white illumination light by receiving drive power from a lamp power source, such as a xenon lamp, a metal halide lamp, a mercury lamp, or a halogen lamp. The light source unit 230 is configured so that the illumination light emitted from the high-intensity lamp is condensed by a condensing lens (not illustrated) and then incident on an incident end of a light carrying bundle (LCB) 102, which is a bundle of optical fibers, via a dimmer (not illustrated).

Alternatively, the light source unit 230 includes a plurality of light emitting diodes that emit light in a wavelength band of a predetermined color. The light source unit 230 is configured so that the light emitted from the light emitting diode is synthesized using an optical element such as a dichroic mirror, and the combined light is condensed as the illumination light by the condensing lens (not illustrated) and then is incident on the light carrying bundle (LCB) 102 of the electronic scope 100. A laser diode can also be used instead of the light emitting diode. The light emitting diode and the laser diode have features such as low power consumption and a low heat value as compared with other light sources, and therefore have a merit that a bright image can be acquired while suppressing the power consumption or the heat value. By acquiring the bright image, it is possible to improve the accuracy of the evaluation value related to inflammation, which will be described later.

Note that in the example illustrated in FIG. 1, the light source unit 230 is built in the processor 200 for an electronic endoscope, but may be provided in the electronic endoscope system 1 as a device separate from the processor 200 for an electronic endoscope. Further, the light source unit 230 may be provided at a distal end of the electronic scope 100 to be described later. In this case, the LCB 102 that guides the illumination light is unnecessary.

The illumination light incident on the LCB 102 from the incident end propagates in the LCB 102, is emitted from the end of the LCB 102 arranged in the distal end of the electronic scope 100, and is irradiated to the biological tissue inside the organ which is a subject via a light distribution lens 104. The reflected light from the biological tissue forms an optical image on a light receiving surface of an image sensor 108 via an objective lens 106.

The image sensor 108 is, for example, a single-plate color charge-coupled device (CCD) image sensor in which various filters of an infrared (IR) cut filter 108a and a Bayer array color filter 108b are arranged on the light receiving surface, and generates primary color signals of red (R), green (G), and blue (B) according to the optical image formed on the light receiving surface. Instead of the single-plate color CCD image sensor, a single-plate color complementary metal oxide semiconductor (CMOS) image sensor can also be used. The electronic scope 100 captures an image of the biological tissue inside the organ using the image sensor 108 and generates the moving image.

A driver signal processing circuit 112 is provided inside a connection portion of the electronic scope 100 with the processor 200. The driver signal processing circuit 112 generates image signals (luminance signal Y and color difference signals Cb and Cr) by performing predetermined signal processing such as color interpolation and matrix calculation on the primary color signals input from the image sensor 108, and outputs the generated image signals to the image processing unit 220 of the processor 200 for an electronic endoscope. Further, the driver signal processing circuit 112 accesses the memory 114 and reads unique information of the electronic scope 100. The unique information of the electronic scope 100 recorded in the memory 114 includes, for example, the number of pixels or sensitivity of the image sensor 108, a frame rate that can be operated, a model number, and the like. The driver signal processing circuit 112 outputs the unique information read from the memory 114 to the system controller 202.

The system controller 202 performs various calculations based on the unique information of the electronic scope 100 and generates a control signal. The system controller 202 uses the generated control signal to control the operation or timing of each circuit in the processor 200 for an electronic endoscope so that processing suitable for the electronic scope 100 which is being connected to the processor 200 for an electronic endoscope are performed.

The timing controller 206 supplies a clock pulse to a driver signal processing circuit 112, an image processing unit 220, and a light source unit 230 according to the timing control by the system controller 202. The driver signal processing circuit 112 drives and controls the image sensor 108 at a timing synchronized with the frame rate of the image processed on the processor 200 for an electronic endoscope side according to the clock pulse supplied from the timing controller 206.

The image processing unit 220 is a unit that can perform image processing according to the surgeon or operator's instruction or a preset processing content. Under the control of the system controller 202, the image processing unit 220 generates a video signal for displaying the image or the like captured by the electronic scope 100 on a monitor based on the image signal of the captured image input from the driver signal processing circuit 112, and outputs the generated video signal to the monitor 300. In addition, the image processing unit 220 processes the plurality of captured images of biological tissue as part of image processing to evaluate an extent of a lesion of an organ, generates the video signal for displaying the evaluation result on the monitor, and outputs the generated video signal to the monitor 300. Specifically, the image processing unit 220 calculates the image evaluation value to be described later, which indicates the extent of the lesion of the biological tissue in each image, from the plurality of images of the biological tissue obtained by the electronic scope 100. Note that the electronic scope 100 captures an image of the biological tissue inside the organ at the set frame rate while moving approximately continuously along the depth direction inside the organ (partially including the case where the image-captured position in the depth direction shifts in the opposite direction). Therefore, the image processing unit 220 uses the image evaluation values of images captured in substantially order along the depth direction according to the surgeon or operator's instruction and the information on the image-captured position inside the organ that is obtained by capturing each of the plurality of images to calculate the representative evaluation values of the image evaluation values for each of the plurality of sections obtained by dividing the region inside the captured organ at a predetermined interval, and uses the representative evaluation value to evaluate the spread of the lesions which are continuously spreading in the depth direction inside the organ.

Further, the image processing unit 220 generates a color map image in which colors of each pixel in the image are replaced according to the pixel evaluation value to be described later. The image processing unit 220 generates information on the evaluation result of the extent of the lesion in the organ and a video signal for displaying the color map image on the monitor, and outputs the information and the video signal to the monitor 300. As a result, the surgeon or operator can receive the evaluation of the extent of the lesion spreading in the depth direction of the organ of interest through the image displayed on the display screen of the monitor 300. The image processing unit 220 outputs the color map image and the information on the evaluation result of the extent of the lesion in the organ to the printer 400 as needed.

The processor 200 for an electronic endoscope is connected to a server 600 via a network interface card (NIC) 210 and a network 500. The processor 200 for an electronic endoscope can download information (for example, electronic medical chart information on a patient, information on a surgeon, and an evaluation result of an extent of a lesion in the same organ in the past) on an endoscopic examination from the server 600. The downloaded information is displayed, for example, on the display screen of the monitor 300 or the operation panel 208. In addition, the processor 200 for an electronic endoscope can upload the evaluation results of the endoscopic examination (endoscopic image data, examination conditions, evaluation result of the extent of the lesion of the organ, surgeon's opinion, and the like) to the server 600, and save the uploaded evaluation results in the server 600.

Figure 2:
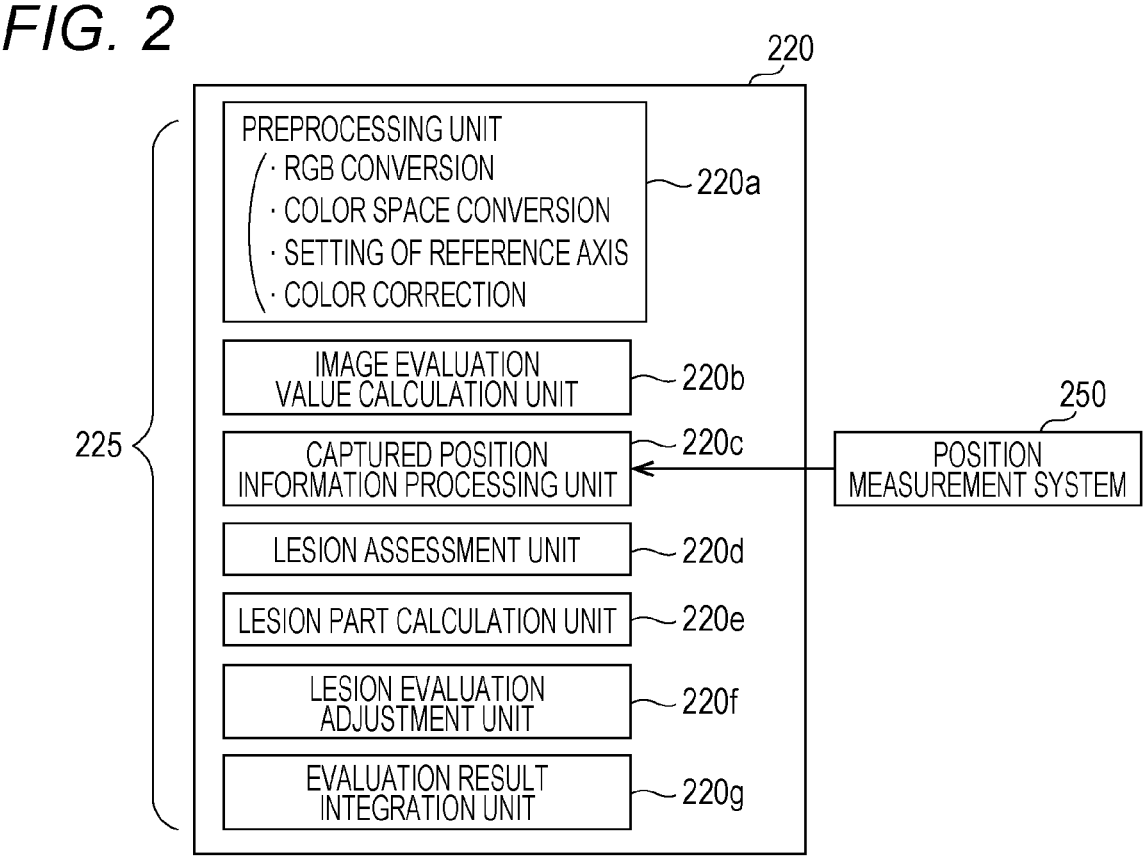
FIG. 2 is a diagram for explaining a configuration of a part of an image processing unit illustrated in FIG. 1 which evaluates a spread of a lesion in a depth direction of an organ.

FIG. 2 is a diagram illustrating the configuration of the part of the image processing unit 220 that evaluates the spread of the lesion in the depth direction of the organ. The image processing unit 220 is a unit configured to process the plurality of images of the biological tissue captured by the electronic scope 100 and evaluate the extent of the lesion. The image processing unit 220 includes a preprocessing unit 220a, an image evaluation value calculation unit 220b, an image-captured position information processing unit 220c, a lesion evaluation unit 220d, a lesion part position calculation unit 220e, a lesion evaluation adjustment unit 220f, and an evaluation result integration unit 220g. The preprocessing unit 220a, the image evaluation value calculation unit 220b, the image-captured position information processing unit 220c, the lesion evaluation unit 220d, the lesion part position calculation unit 220e, the lesion evaluation adjustment unit 220f, and the evaluation result integration unit 220g are included in an evaluation unit 225 configured to process a plurality of captured images of biological tissue to evaluate the extent of the lesion of the organ. The preprocessing unit 220a, the image evaluation value calculation unit 220b, the image-captured position information processing unit 220c, the lesion evaluation unit 220d, the lesion part position calculation unit 220e, the lesion evaluation adjustment unit 220f, and the evaluation result integration unit 220g may be a software module formed by starting software stored in the memory 204, and may be configured by hardware.

Further, in the embodiment illustrated in FIG. 2, the image processing unit 220 includes the lesion part position calculation unit 220e, but in another embodiment, does not include the lesion part position calculation unit 220e.

The image evaluation value calculation unit 220b calculates the image evaluation value indicating the extent of lesion in the image of interest, for the plurality of images of interest of at least some of the plurality of images that are obtained by image-capturing different locations of biological tissue within the organ. The image of interest is specified by the input instruction by the surgeon or operator. The input instruction by the surgeon or operator is performed, for example, by pressing a button provided on an operation unit (not illustrated) provided on the electronic scope 100. According to an embodiment, the degree of inflammation, which is an example of a lesion, is evaluated for each image of interest to obtain the image evaluation value. Hereinafter, an example of the lesion including the inflammation that occurs in ulcerative colitis or the like will be described.

The image evaluation value calculation unit 220b uses redness of biological tissue quantizing a degree of red color of the biological tissue for each pixel, as the pixel evaluation value, and integrates the pixel evaluation values of the entire image to calculate values combined into one numerical value as the image evaluation values. That is, the strength of the inflammation of the biological tissue is evaluated by using the degree of red color of the biological tissue. Hereinafter, a form for calculating the redness of biological tissue, which indicates the degree of inflammation, will be described as an example.

The preprocessing unit 220a is a unit that preprocesses an image for evaluating the degree of red color indicated by biological tissue. As illustrated as an example, the preprocessing unit 220a performs each processing of RGB conversion, color space conversion, setting of a reference axis, and color correction.

The preprocessing unit 220a converts the image signals (the luminance signal Y and the color difference signals Cb and Cr) input from the driver signal processing circuit 112 into the image color components (R, G, and B) using a predetermined matrix coefficient.

The preprocessing unit 220a further performs color conversion to orthogonally project the image data converted into the image color component onto an RG plane. Specifically, the image color components of each pixel in an RGB color space defined by the three primary colors of RGB are converted into an image color component of RG. Conceptually, the image color components of each pixel in the RGB color space are plotted in the RG plane (for example, a partition in the RG plane on which the pixel value of the R component pixel=0 to 255 and the pixel value of the G component=0 to 255 are taken). Hereinafter, for convenience of explanation, points of the image color components of each pixel in the RGB color space and points of the image color components plotted in the RG color space are referred to as "pixel correspondence points". The image color components of the RGB, respectively, of the RGB color space are, for example, color components having a wavelength of 620 to 750 nm, a wavelength of 495 to 570 nm, and a wavelength of 450 to 495 nm in order. Note that the color component constitutes a color space (including a color plane). Hue and saturation are excluded from the "color component".

The preprocessing unit 220a sets the reference axis in the RG plane needed to evaluate the redness of biological tissue.

In the biological tissue inside the organ of the patient as the subject, the R component of the image color components is dominant over other components (G component and B component) due to an influence of a hemoglobin pigment and the like. When the extent of the lesion of the lesion part is low and the lesion part is the inflammation part, the stronger the inflammation, the stronger the red color (R component) with respect to other colors (G component and B component). However, the color of the captured image in the organ changes depending on photographing conditions (for example, a lighting condition of the illumination light) that affect the brightness. Illustratively, a shaded portion that the illumination light does not reach is black (an achromatic color, for example, values of the image color components of R, G, and B are zero or a value approximating zero), and a portion where the illumination light is regularly reflected strongly is white (an achromatic color, for example, when the values of the image color components of R, G, and B is 8-bit gradation, the values are 255 or approximates 255). That is, even when the same inflammation part in which inflammation occurs is captured, the pixel value of the inflammation part increases as the illumination light hits strongly. Therefore, depending on the lighting condition of the illumination light, the value of the color component of the image may take a value that does not correlate with the strength of inflammation.

In general, a healthy part inside the organ without the inflammation is covered with sufficient mucous membrane. On the other hand, the inflammation part inside the organ where inflammation is occurring is not covered with sufficient mucous membrane. Specifically, since the blood vessels dilate and blood and body fluids leak from the blood vessels, the mucous membrane becomes relatively thin and the color of the blood becomes easily visible. The mucous membrane is basically white, but the color is slightly yellowish, and the color (yellow) that appears on the image changes depending on the light and shade (thickness of the mucous membrane). Therefore, it is considered that the light and shade of mucous membrane is also one of the indicators for evaluating the degree of inflammation.

Figure 3:
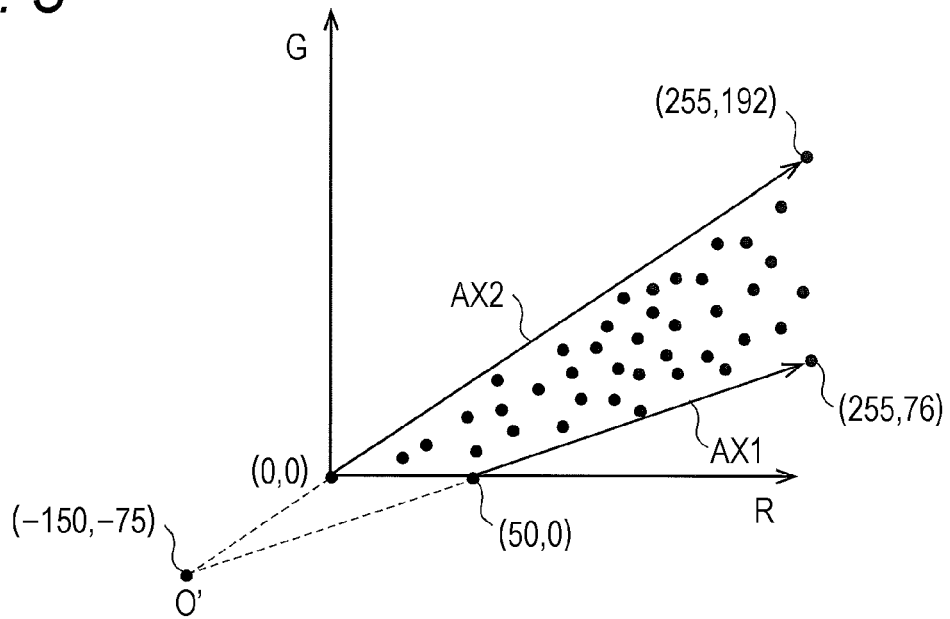
FIG. 3 is a diagram for explaining an example of a reference axis in a color space used in an embodiment.

Therefore, as illustrated in FIG. 3, a straight line passing through (50,0) and (255,76) is set as one of the reference axes in the RG color space, and a straight line passing through (0,0) and (255, 192) is set as one of the reference axes. For convenience of explanation, the former reference axis is referred to as "hemoglobin change axis AX1", and the latter reference axis is referred to as "mucous membrane change axis AX2". FIG. 3 is a diagram for explaining an example of the reference axis in the color space used in an embodiment.

The plot illustrated in FIG. 3 is one obtained from a result of analyzing a large number of reference images inside the organ. The reference images used for the analysis include an inflammation image example at each stage such as an inflammation image example (an inflammation image example with the most severe level) with the highest degree of inflammation or an inflammation image example with the lowest degree of inflammation (substantially considered to be a healthy part). Note that in the example illustrated in FIG. 3, only a part of the plot obtained as the result of the analysis is illustrated for the sake of clarifying the drawing. The actual number of plots obtained as the result of the analysis is much larger than the number of plots illustrated in FIG. 3.

As described above, the stronger the inflammation, the stronger the R component of the color components of the image with respect to the other components (G component and B component). Therefore, in a boundary line between a region where the plot is distributed and a region where the plot is not distributed, an axis on the boundary line closer to the R axis than the G axis, in the example illustrated in FIG. 3, an axis on the boundary line passing through (50,0) and (255, 76) is set as an axis having a high correlation with a part having the strongest degree of inflammation, that is, a high correlation with a part having the highest degree of inflammation. This axis is the hemoglobin change axis AX1. The hemoglobin change axis AX1 is superposed with plots corresponding to the highest degree of inflammation captured under various photographing conditions, for example, the lighting conditions of illumination light. Therefore, the hemoglobin change axis AX1 is the axis on which the pixel correspondence points plotted converges as the degree of inflammation of the biological tissue increases.

On the other hand, the closer to the healthy part, the stronger the G component (or B component) of the color components of the image with respect to the R component. Therefore, in the boundary line between the region where the plot is distributed and the region where the plot is not distributed, an axis on the boundary line closer to the G axis than the R axis, in the example illustrated in FIG. 3, an axis on the boundary line passing through (0.0) and (255,192) is a part having the lowest degree of inflammation, that is, a part having the lowest degree of inflammation, and is set as an axis having a high correlation with one substantially considered to be the healthy part. This axis is the mucous membrane change axis AX2. The mucous membrane change axis AX2 is superposed with plots corresponding to the lowest degree of inflammation captured under various photographing conditions, for example, the lighting conditions of illumination light, that is, one substantially considered to be the normal part. Therefore, the mucous membrane change axis AX2 is the axis on which the pixel correspondence points to be plotted converge as the degree of inflammation decreases (the closer to the healthy part).

In addition, the highest part of the extent of the lesion in the lesion part is accompanied by bleeding. On the other hand, the lowest part of the extent of the lesion is a substantially normal healthy part, and therefore is covered with a sufficient mucous membrane. Therefore, the plot in the RG color space illustrated in FIG. 3 can be considered to be distributed in the region sandwiched between the axis most correlated with blood (hemoglobin pigment) and the axis most correlated with the color of the mucous membrane. Therefore, of the boundary lines between the region where the plot is distributed and the region where the plot is not distributed, the boundary line closer (stronger R component) to the R axis corresponds to the axis (hemoglobin change axis AX1) showing the inflammation part with the highest degree of inflammation, and the boundary line closer (stronger G component) to the G axis corresponds to the axis (mucous membrane change axis AX2) showing the inflammation part with the lowest degree of inflammation.

After setting the reference axis in this way, the processing of calculating the redness of biological tissue indicating the degree of red color, which will be described later, is performed on the color component of the image orthogonally projected. Before the processing of calculating the redness of biological tissue, the color correction is performed on the pixel data orthogonally projected.

Note that the reference axis illustrated in FIG. 3 is an example, and the reference axis varies depending on a type of disease.

The preprocessing unit 220a performs the color correction on the color components of the image represented in the RG color space before calculating the inflammation evaluation value. The correction matrix coefficient is saved in the memory 204. Despite the same inflammation part, to prevent the inflammation evaluation value to be described later from varying when captured by different electronic endoscope systems (in other words, to suppress inter-individual error in the electronic scope), the preprocessing unit 220a corrects pixel data (R, G), which is the pixel corresponding points in the RG color space of each pixel, as illustrated in the following equation using the correction matrix coefficient.

$$\begin{pmatrix} R_{new} \\ G_{new} \end{pmatrix} = \begin{pmatrix} M_{00} & M_{01} \\ M_{10} & M_{11} \end{pmatrix} \begin{pmatrix} R \\ G \end{pmatrix}$$

$R_{new}$: Corrected pixel data (R component)
$G_{new}$: Corrected pixel data (G component)
$M_{00}$ to $M_{11}$: Correction matrix coefficient
R: Pixel data before correction (R component)
G: Pixel data before correction (G component)

Figure 4:
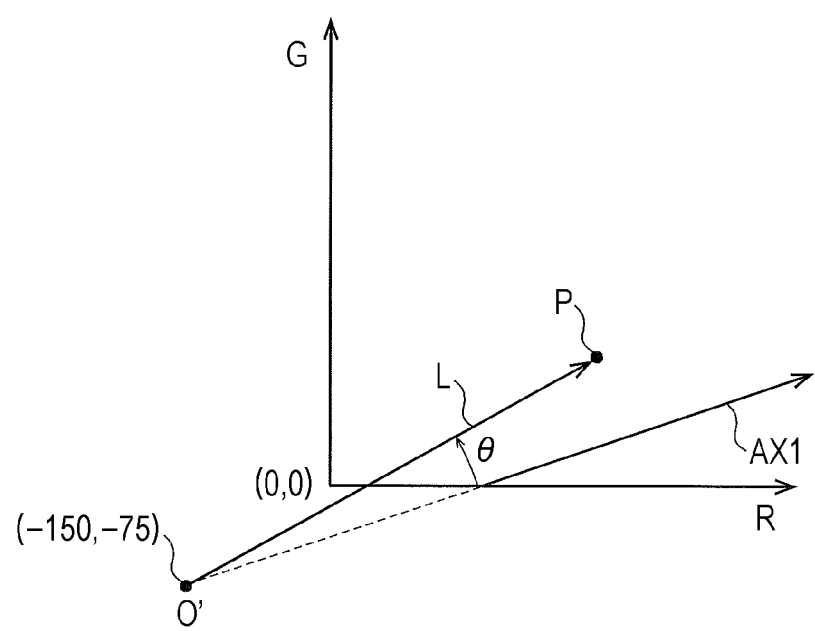
FIG. 4 is a diagram for explaining a method of calculating a deviation angle for calculating redness of biological tissue used in an embodiment.

The image evaluation value calculation unit 220b selects one pixel of interest from the pixels and calculates a deviation angle for calculating the degree of inflammation for the selected pixel of interest based on the information on the color component of the pixel of interest. That is, the quantification process is performed to quantify the degree of red color of the biological tissue based on the information on the color component of the pixel. FIG. 4 is a diagram for explaining a method of calculating a deviation angle for calculating redness of biological tissue used in an embodiment. Specifically, as illustrated in FIG. 4, the image evaluation value calculation unit 220b sets an intersection of the hemoglobin change axis AX1 and the mucous membrane change axis AX2 as a reference point O', and calculates the deviation angle θ in which a direction of a line segment L connecting the reference point O' and the pixel corresponding point P of the pixel of interest deviates from the reference axis AX1. Note that the reference point O' is located at coordinates (−150, −75). The example in which the reference point O' is set to the coordinates (−150, −75), but is not limited thereto. The reference point O' can change as appropriate, and may be, for example, the intersection of the R axis and the G axis in the RG color space.

An appropriate coordinate position as the reference point O' is, for example, a position where the error of the evaluation result due to the fluctuation of the brightness can be reduced. Specifically, the reference point O' is preferably set in advance a point where the error between the evaluation result in a dark part (brightness is less than the predetermined value) and the evaluation result in a non-dark part (brightness is equal to or greater than the predetermined value) is minimized Also, for example, if the reference point O' is set between coordinates (−10, −10) and (10,10), compared with the case where the coordinates (−150, −75) and the like are set as the reference point O', the amount of change in the angle θ in the case where the pixel correspondence point changes is larger, so the resolution is improved. As a result, the highly accurate evaluation result can be obtained.

On the other hand, by setting the reference point O' between the coordinates (−50, −50) and (−200, −200), the evaluation result indicating the degree of inflammation is less affected by noise.

When the brightness of the photographed image of the biological tissue inside the organ changes depending on the lighting condition of the white light, the color of the image is affected by individual differences, a photographing location, a state of inflammation, and the like, but in the RG color space, generally, the inflammation part with the highest level of severity changes along the hemoglobin change axis AX1, and the inflammation part with the lowest degree of inflammation changes along the mucous membrane change axis AX2. In addition, it is estimated that the color of the image of the inflammation part with the intermediate degree of inflammation changes with the same tendency. That is, when the pixel corresponding point corresponding to the inflammation part changes by the lighting condition of the illumination light, the pixel corresponding point shifts in an azimuth direction starting from the reference point O'. In other words, when the pixel corresponding point corresponding to the inflammation part changes by the lighting condition of the illumination light, the deviation angle θ with respect to the mucous membrane change axis AX2 moves constantly, and the distance from the reference point O' changes. This means that the deviation angle θ is a parameter that is substantially unaffected by the change in the brightness of the image.

The smaller the deviation angle θ, the stronger the R component with respect to the G component, which indicates that the degree of red color in the lesion part is relatively large. In addition, the larger the deviation angle θ, the stronger the G component with respect to the R component, which indicates that the degree of red color is relatively small. Therefore, the image evaluation value calculation unit 220b normalizes the angle θ so that the value becomes 255 when the deviation angle θ is zero and the value becomes zero when the deviation angle θ is a maximum angle, that is, $\theta_{MAX}$. Note that $\theta_{MAX}$ is equal to the angle formed by the hemoglobin change axis AX1 and the mucous membrane change axis AX2. That is, the image evaluation value calculation unit 220b sets the value in the range of 0 to 255 obtained by normalizing the deviation angle θ calculated based on the information of the color component of each pixel of interest for each pixel of interest to the redness of biological tissue (pixel evaluation value).

Note that the pixel of interest is selected one by one for all the pixels of the image.

Note that in the example illustrated in FIG. 4, the RG color space is used as the color space, but the RB color space can be used instead of the RG color space.

The image evaluation value calculation unit 220b calculates the redness of biological tissue, which is a normalized value of the deviation angle θ, as the pixel evaluation value, but in some cases, the whiteness of biological tissue, which indicates the degree of feature of the ulcer of the biological tissue, can also be calculated as an evaluation value. For example, a gain adjustment that assigns a linear gain to the pixel value of each color component of each pixel of biological tissue image is performed, and tone enhancement processing that substantially widens a dynamic range near a color gamut peculiar to lesion to increase an effective resolution of color representation, and thus, an ulcer part containing white moss and purulent mucus of ulcerative colitis indicates white and the inflammation part showing red color containing edema and easy bleeding or the normal part showing yellow or green color can be distinguished by the color component. As illustrated in FIG. 4, the whiteness of biological tissue can be calculated using the deviation angle with respect to a reference axis different from the hemoglobin change axis AX1, which is displayed on the color space that is the coordinate axis of the two color components (two of the R, G, and B components) or the three color components (the R, G, and B components). Note that the tone enhancement processing is performed by the preprocessing unit 220a.

The image evaluation value calculation unit 220b calculates one image evaluation value using the pixel evaluation value of each pixel. For example, in the captured image, the pixels representing the image of the biological tissue to be evaluated are selected, and the integrated value or the average value of the pixel evaluation values of the selected pixels is calculated as one image evaluation value. Alternatively, for example, by extracting the pixels to be evaluated based on the color component or the brightness component in a predetermined range from the RGB color component for each pixel or the brightness component of the pixel and obtaining the average value of the pixel evaluation values of the extracted pixels, obtaining a weighted average value using a predetermined weighting coefficient, or performing integration processing, the image evaluation value calculation unit 220b calculates one image evaluation value. It is preferable that the pixel portion to be evaluated in the image is a portion having a value of a color component within a predetermined range assumed in the biological tissue in order to evaluate the degree of inflammation of the organ with high accuracy, and is a pixel portion having the brightness component equal to or greater than the predetermined value illuminated by the illumination light.

The image evaluation value calculated by the image evaluation value calculation unit 220b is transmitted to the lesion evaluation unit 220d.

The image evaluation value calculation unit 220b further creates a color map image in which the image of the biological tissue is mosaicked with a display color that changes according to the redness of biological tissue. A table in which the pixel evaluation value and the predetermined display color are associated with each other is stored in a storage area of the memory 204 in order to create the color map image. In the above table, for example, different display colors are associated with each value in increments of 5. Illustratively, blue is associated in the range where the pixel evaluation value is 0 to 5, different display colors are associated according to the order of colors in a color circle every time the pixel evaluation value increases by 5, and red is associated in the range where the pixel evaluation value is 250 to 255. The display color is a color that approaches a warm color from a cold color, for example, from blue to yellow to red as the redness of biological tissue is larger. The image evaluation value calculation unit 220b determines the display color of the selected pixel of interest on the color map image according to the redness of biological tissue of the pixel of interest based on the above table.

In this way, the image evaluation value calculation unit 220b creates a color map image in which colors are assigned according to the redness of biological tissue.

The image-captured position information processing unit 220c acquires the information on the image-captured position transmitted from the position measurement system 250 provided in the electronic endoscope system 1, and associates the acquired position information with the captured image of interest. The position measurement system 250 is a system that uses a sensor to acquire, for example, the position of the image sensor 108 located at the distal end of the electronic scope 100 inserted into the organ, and furthermore each position of subsequent flexible tubes, a system that acquires an insertion length of the inserted electronic scope 100 from the opening end of the organ, or a system that allows a surgeon who sees the captured image displayed on the monitor 300 to acquire a specific part passing signal by pressing a button generating the specific part passing signal indicating that the distal end of the electronic scope 100 passes through a feature part in the inserted organ.

The acquired information of the image-captured position associated with the image of interest is sequentially transmitted to the lesion evaluation unit 220*d*.

In a system that acquires the position of the image sensor 108 using the sensor, for example, a plurality of magnetic sensors are provided in the position near the image sensor 108 of the distal end of the electronic scope 100 and in the flexible tube subsequent to the side of the processor 200 from the distal end at a predetermined interval, and the electronic scope 100 can apply a magnetic field with different strength depending on the position from the outside of the human body inserted into the organ, know the position of the magnetic sensor provided at the distal end by measuring the strength of the magnetic field with the magnetic sensor, and furthermore, and know the curved shape of the flexible tube in the organ from the positions of the plurality of magnetic sensors. As a result, it is possible to know the position of the distal end of the image sensor 108, the shape of the electronic scope 100 in the organ, and furthermore, the insertion length of the electronic scope 100 from the opening end of the organ.

In the case of the system that acquires the insertion length of the electronic scope 100 inserted from the opening end of the organ, for example, by acquiring the extent to which the biological tissue moves between images with an adjacent capture time in the captured moving image using optical flow processing and by integrating the acquisition results to calculate the moving distance, it is possible to acquire the information on the insertion length of the current electronic scope 100. Further, for example, by measuring the extended length of the flexible tube following from the distal end of the inserted electronic scope 100 into the organ, it is possible to acquire the information on the insertion length of the current electronic scope 100.

In the system that acquires the specific part passing signal of the organ, by pressing a button of an operation unit with a surgeon's or operator's hand when the identifiable specific part inside the organ appears in the image and passes therethrough while the surgeon is looking at the image displayed on the monitor 300, it is possible to generate the specific part passing signal and for the image-captured position information processing unit 220*c* to acquire the specific part passing signal. The position of the specific part inside the organ includes, for example, a position where an ascending colon begins, a position where the ascending colon ends, the large intestine is bent, and a transverse colon begins, a position where the transverse colon ends, the large intestine is bent, and the descending colon begins, a position where the descending colon ends, the large intestine is bent, and a sigmoid colon begins, a position where the sigmoid colon ends and a rectum begins, and a position where the rectum ends and reaches an anus, when the organ is the large intestine.

The lesion evaluation unit 220*d* uses the information on the image-captured position transmitted from the image-captured position information processing unit 220*c* to calculate the representative evaluation value of the image evaluation value from the image evaluation values of the plurality of images of the biological tissue captured within the plurality of sections, respectively, for each of the plurality of sections obtained by dividing the region inside the captured organ at the predetermined interval. Furthermore, the lesion evaluation unit 220*d* evaluates the spread of the lesions that are continuously spreading in the depth direction inside the organ by using the representative evaluation value. For example, in the case of ulcerative colitis in a large intestine, it can be evaluated that the lesion is spreading from the rectum to the descending colon. In such an evaluation, the spread of the lesion can be evaluated assuming that the region in which the representative evaluation value exceeds a preset threshold value is the lesion part.

Here, the section may be one defined in advance by the surgeon, or the section may be divided by the specific part passing signal. When a section is defined by the specific part passing signal, the section is called a segment.

This segment is a part that can be identifiably distinguished from other parts in one organ, for example, when the organ is a large intestine, the organ includes a segment of ascending colon, a segment of transverse colon, a segment of descending colon, a segment of sigmoid colon, a segment of rectum, and the like. In such segments, the section is divided by the specific part passing signal.

According to an embodiment, it is preferable that the representative evaluation value calculated by the lesion evaluation unit 220*d* from the image evaluation value is a statistic of the image evaluation values (hereinafter, this image evaluation value is referred to as the image evaluation values belonging to each section) of the plurality of captured images of biological tissue included in each section.

By capturing an image of the biological tissue while moving the electronic scope 100 inside the organ, it is possible to evaluate the spread of the lesions that are continuously spreading in the depth direction inside the organ by obtaining the representative evaluation value for each section.

The statistic preferably includes the average value, the median value, the most frequent value, or the maximum value. According to an embodiment, it is more preferable to use the maximum value from the viewpoint that the strength of the lesion can be optimally shown in the statistic.

According to an embodiment, the lesion evaluation unit 220*d* is configured to divide and evaluate the extent of the lesion in a plurality of ranks related to the strength of lesion, and it is preferable that the lesion evaluation unit 220*d* defines one of a plurality of ranks based on the representative evaluation value and evaluates the extent of the lesion for each section by the ranks. As a result, it is possible for a surgeon to accurately know the spread and strength of the lesions that are continuously spreading in the depth direction inside the organ.

Further, according to an embodiment, it is preferable that the lesion evaluation unit 220*d* assesses the presence or absence of the lesion part in which the lesion extends continuously in the depth direction of the organ for each section based on the representative evaluation value. The region of the lesion part is the region in which the representative evaluation value is greater than the preset threshold value.

According to an embodiment, the lesion evaluation unit 220*d* can assess the presence or absence of the lesion part in which the lesion extends continuously in the depth direction of the organ based on the image evaluation value. The region of the lesion part is the region in which the image evaluation value is greater than the preset threshold value. Since the image evaluation value is an evaluation value for each image, the image evaluation value may include a noise component. In this case, it is preferable to use the representative evaluation values for each section instead of the image evaluation value.

The lesion part position calculation unit 220*e* obtains a start position and an end position of the region of the lesion part by obtaining the section in which the lesion part is located among the above sections based on the position information on the captured image, and specifies the position of the lesion part. In order to accurately determine the start position and end position of the lesion part, it is also preferable to determine the position where the image evaluation value crosses a preset threshold value by using the image evaluation value and the information on the position where the image is captured. In this case, the lesion part position calculation unit 220e compares the threshold value with each image evaluation value and assesses whether the image evaluation value crosses the threshold value. The assessment result is transmitted to the lesion evaluation unit 220d. At this time, it is preferable that the lesion evaluation unit 220d calculates the length of the lesion part from the information on the start position and the end position of the lesion part obtained by the lesion part position calculation unit 220e.

Therefore, according to an embodiment, the lesion part position calculation unit 220e is configured to set the position where the image evaluation value crosses the preset threshold value with the movement of the image-captured position of the image as the start or end position of the lesion part to specify the position of the start or end position of the lesion part in the organ from the information on the image-captured position of the image, and the lesion evaluation unit 220d may be configured so that even if the electronic scope 100 is inserted into the deepest portion of the depth direction in the organ in which it is preferable to calculate the length of the depth direction in the organ of the lesion part from the specific result, the lesion part may further continue inside. In this case, since the lesion part already exists at the image-captured position of the deepest portion in the depth direction, the length of the lesion part in the depth direction is referred to as a length from the image-captured position of the deepest portion in the depth direction with the image evaluation value to the end position. It is preferable that the monitor 300 displays at least one of the end position and/or start position of the lesion part, and the length of the lesion part on the screen. This makes it easier for the surgeon to recognize the spread of the lesion in the depth direction of the organ.

In addition, it is preferable that the lesion evaluation unit 220d obtains the total value of the representative evaluation values corresponding to the sections included between the start position and the end position of the lesion part among the sections, and evaluates the extent of the lesion based on this total value. This makes it possible to evaluate the spread of the lesion in the depth direction of the organ and the extend (strength) of lesion (strength) at the same time. In this case, for example, the total value can be divided into a plurality of levels and the extent of the lesion can be evaluated according to the level.

In the graph showing the position information (for example, the distance from the insertion deepest portion of the electronic scope to the opening end) along the depth direction of each section on the horizontal axis and the representative evaluation value on the vertical axis when the lesion evaluation unit 220d narrows the interval between predetermined sections and sets many sections, the curve created by the representative evaluation values for each section may be uneven in adjacent sections. In this case, according to an embodiment, it is preferable that the curve of the representative evaluation value shown in the above graph is processed smoothly by performing moving average processing or curve fitting processing using a function indicating a predetermined curve by using the position information of the section and the representative evaluation value.

The representative evaluation value calculated by the lesion evaluation unit 220d is generated for each section, but there is no image evaluation value calculated from the image captured by the surgeon or operator's instruction among the plurality of sections, and there may be an empty section in which the representative evaluation value is not generated. For the empty section, the lesion evaluation adjustment unit 220f defines an estimated representative evaluation value based on one of the image evaluation values in the non-empty section located on the back side of the organ from the empty section or the representative evaluation value in the non-empty section located on the back side of the organ from the empty section, and assigns the estimated representative evaluation value to the empty section. The estimated representative evaluation value may be the representative evaluation value in the non-empty section located on the back side of the organ from the empty section. Note that the non-empty section is referred to as the section in which the representative evaluation value is generated.

Alternatively, for the empty section, the lesion evaluation adjustment unit 220f sets two of the representative evaluation values in each non-empty section which has the empty section sandwiched between both sides thereof as the reference evaluation value, and assigns the composite representative evaluation value obtained based on the reference evaluation value to the empty section as the estimated representative evaluation value indicating the extent of the lesion in the empty section.

Alternatively, for the empty section, the lesion evaluation adjustment unit 220f calculates the composite representative evaluation value indicating the extent of the lesion as the estimated representative evaluation value based on the representative evaluation values in the non-empty sections which have the empty section sandwiched between both sides thereof and assigns the estimated representative evaluation value to the empty section. In this case, the lesion evaluation adjustment unit 220f calculates the estimated representative evaluation value in the empty section by the interpolation by the curve fitting using the length information of each of the non-empty sections on both sides and the length information of the empty section, and the representative evaluation values.

In this way, since the estimated representative evaluation value can be set in the empty section using the lesion evaluation adjustment unit 220f, when the spread of the lesion is examined at a later date in addition to being able to evaluate the spread of the lesion in the depth direction of the organ, it is possible to evaluate the conditions of progress or retreat in the depth direction of the organ in the biological tissue. A specific description of the estimated representative evaluation value will be described later.

The evaluation result integration unit 220g integrates the information indicating the spread of the lesion part in the depth direction, the information on the start position/the end position of the lesion part, or the length of the lesion part, and the information on the ranked strength of the lesion parts for each section, and displays the integrated information on the monitor 300 as one or more evaluation result screen in a graph showing numerical values of the representative evaluation values or the estimated representative evaluation value for each section, which is the evaluation result, or a distribution of the representative evaluation values in each section or the section of the estimated representative evaluation value.

Figure 5:
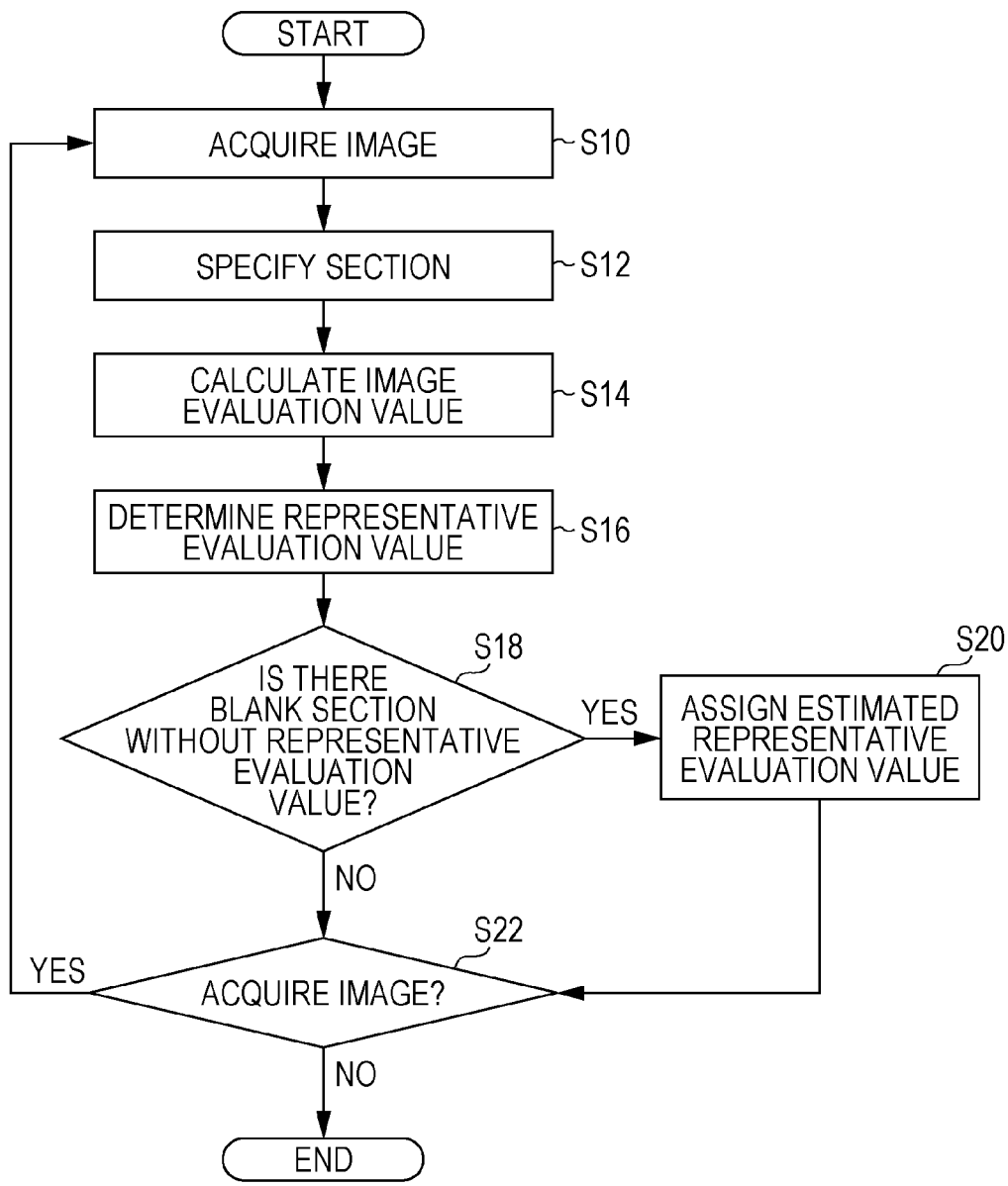
FIG. 5 is a diagram illustrating an example of a flow from image acquisition to obtaining representative evaluation values for each section performed by an evaluation unit of the embodiment.

FIG. 5 is a diagram illustrating an example of a flow from image acquisition to obtaining a representative evaluation values for each section performed by the image processing unit 220.

First, the preprocessing unit 220a acquires an image (step S10) and performs the above-described processing. At this time, the image-captured position information processing unit 220c from the position measurement system 250 acquires the information on the image-captured position of the acquired image in association with the captured image. As a result, the lesion evaluation unit 220d uses the image-captured position information to specify the section in which the acquired image is captured in the organ among the predetermined sections (step S12). On the other hand, the image evaluation value calculation unit 220b calculates the image evaluation value using the image processed by the preprocessing unit 220a (step S14).

Note that step S14 is not limited to being performed after step S12, and can be performed before or at the same time as step S12.

The lesion evaluation unit 220d determines the representative evaluation value from the calculated image evaluation value (step S16). The representative evaluation value is the image evaluation value when there is one image evaluation value, and is the statistic of the image evaluation value for each section such as the average value, the median value, the most frequent value, or the maximum value when there are two or more image evaluation values. The maximum value is more suitable for the evaluation of the lesion because the extent of the lesion is the strongest in the section. Further, the representative evaluation value may be the image evaluation value calculated at the end of each section when the representative evaluation value is calculated while playing back the image.

The lesion evaluation adjustment unit 220f assesses whether or not there is an empty section in which there is no image evaluation value and there is the empty section in which the representative evaluation value is not generated (step S18). When there is the empty section, the lesion evaluation adjustment unit 220f determines the estimated representative evaluation value by the above-mentioned processing, and assigns the estimated representative evaluation value to the empty section (step S20).

Further, the preprocessing unit 220a assesses whether or not to acquire an image for evaluating the lesion by the surgeon or operator's instruction (step S22). The preprocessing unit 220a waits for image acquisition until no more images are acquired.

Figure 6:
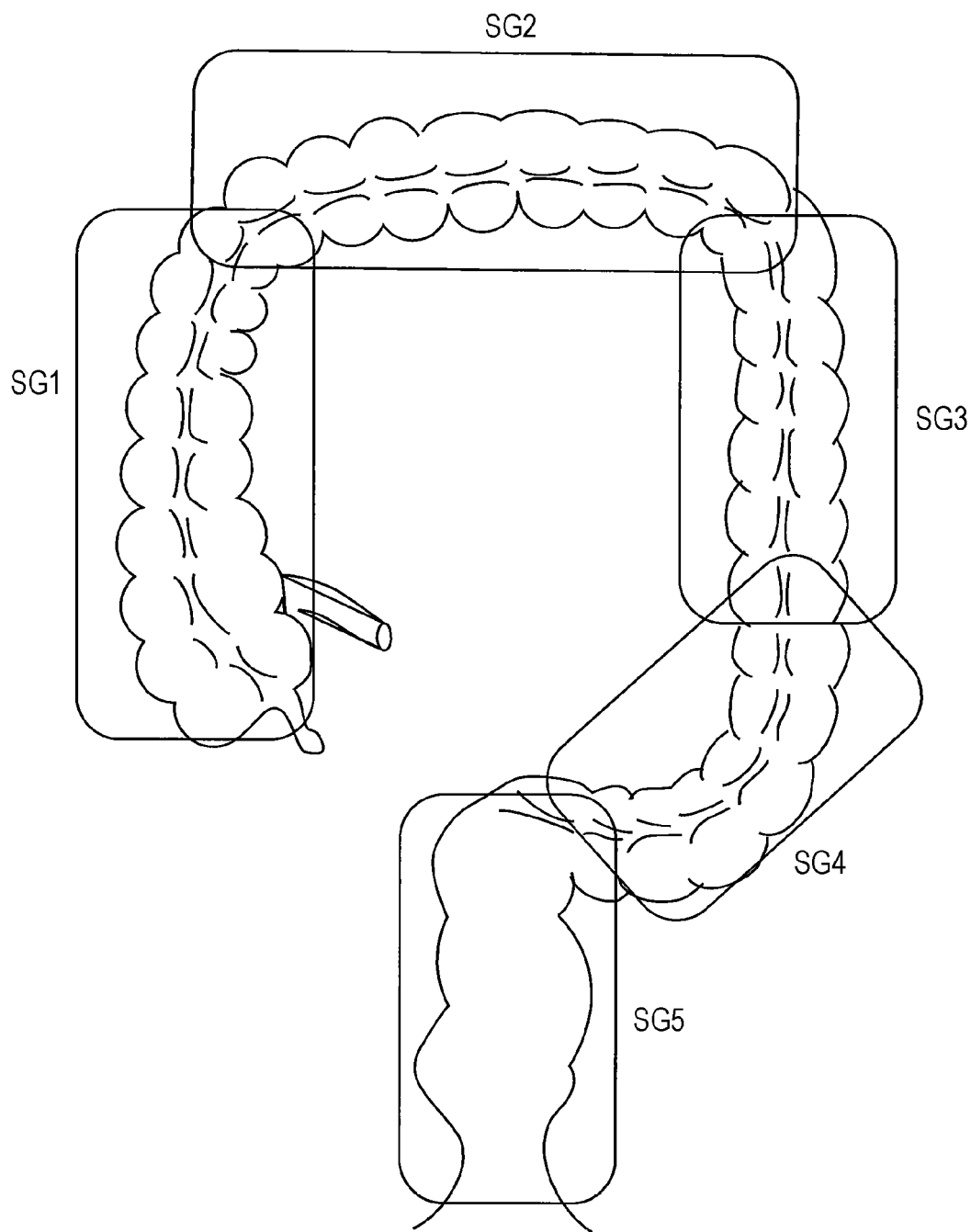
FIG. 6 is a diagram for explaining a large intestine which is an example of the organ to be measured by the endoscope system of the embodiment.

FIG. 6 is a diagram illustrating a large intestine, which is an example of an organ. The large intestine includes a rectum, sigmoid colon, descending colon, transverse colon, and ascending colon, in order from the opening end (anus). Hereinafter, the rectum is referred to as segment SG5, the sigmoid colon is referred to as segment SG4, the descending colon is referred to as segment SG3, the transverse colon is referred to as segment SG2, and the rectum is referred to as segment SG1.

Generally, the electronic scope 100 is inserted up to the deepest portion of the segment SG1 which is the ascending colon, and then moves toward the opening end side so as to be pulled out. Therefore, the electronic scope 100 captures images in the order of segment SG1, the segment SG2, the segment SG3, and . . . .

Figure 7:
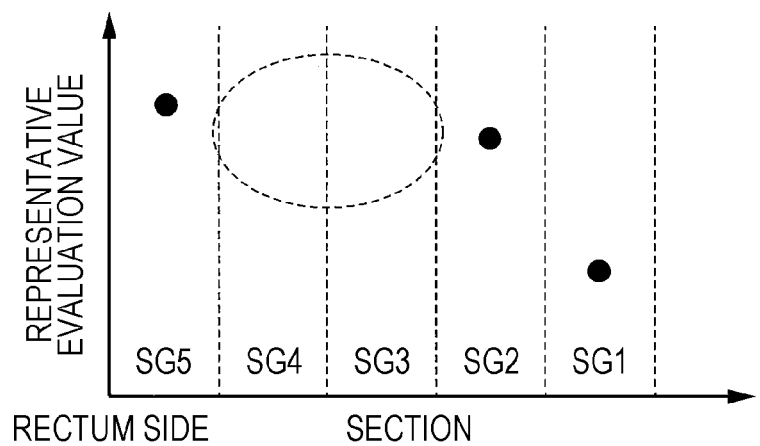
FIG. 7 is a diagram illustrating an example of an evaluation result by the conventional lesion evaluation unit.

FIG. 7 is a diagram illustrating an example of the conventional evaluation result. The evaluation result illustrated in FIG. 7 is a graph in which the horizontal axis represents the position from segment SG5 to segment SG1 and the vertical axis represents the representative evaluation value. In the example illustrated in FIG. 7, the representative evaluation values of the segment SG5 and the segment S2 are high, and the occurrence of inflammation in the segment SG5 and the segment S2 is shown. The segments SG3 and SG4 are empty sections without the representative evaluation value.

Figure 8:
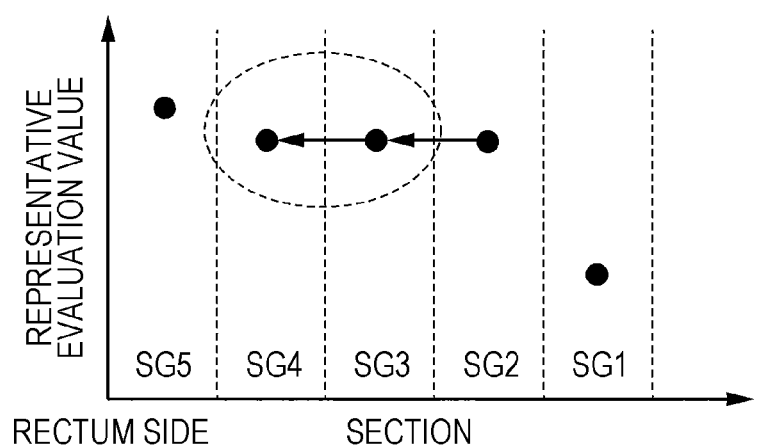
FIG. 8 is a diagram illustrating another example of the adjustment of the evaluation result by the lesion evaluation adjustment unit of the embodiment.

FIG. 8 is a diagram illustrating an example of the adjustment of the evaluation result by the lesion evaluation adjustment unit 220f. Similar to FIG. 7, the result illustrated in FIG. 8 is a graph in which the horizontal axis represents the position from the segment SG5 to the segment 1 and the vertical axis represents the representative evaluation value. In the example illustrated in FIG. 8, the lesion evaluation adjustment unit 220f assigns the estimated representative evaluation values to the segments SG3 and SG4, which are empty sections. In the example illustrated in FIG. 8, the lesion evaluation adjustment unit 220f assigns the estimated representative evaluation value in the segment SG2 which is the non-empty section located on the back side of the organ from the empty section to the segments SG3 and SG4 of the empty section, for the empty section (segments SG3 and SG4) in which the representative evaluation value is not generated.

As illustrated in FIG. 8, even if there are two or more empty sections in a row, the representative evaluation value in the segment SG2, which is a non-empty section located on the back side of the organ from the empty section is assigned to the segments SG3 and SG4 as the estimated representative evaluation value. In this way, by diverting the representative evaluation value in the segment SG2, which is a non-empty section located on the back side of the organ from the empty section as the estimated representative evaluation value of the empty section, since the surgeon or operator checks the extent of the lesion by looking at the image displayed on the monitor 300 while moving the electronic scope 100 in the opposite direction (direction from the segment SG1 side to the segment SG5 side) to the back side of the organ, the empty section is highly likely to be a section with a small change from the extent of the lesions in the section on the back side. Therefore, the representative evaluation value in the segment SG2, which is a non-empty section on the back side of the organ from the empty section, can be used as the estimated representative evaluation value in the segments SG3 and SG4 which are the empty section.

Figure 9:
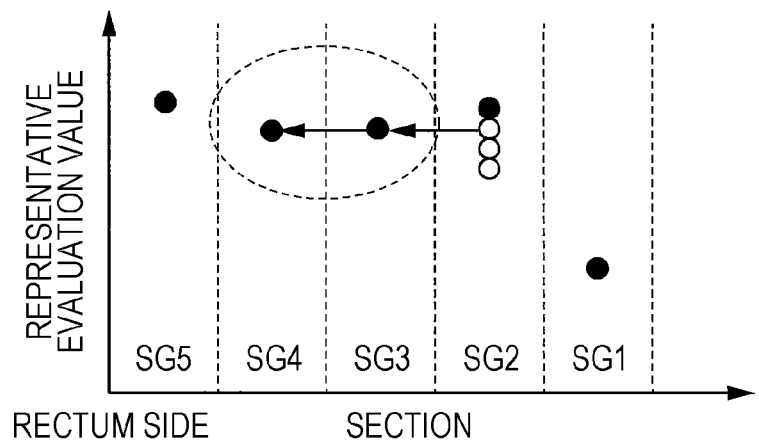
FIG. 9 is a diagram illustrating an example of the adjustment of the evaluation result by the lesion evaluation adjustment unit of the embodiment.

In addition, the lesion evaluation adjustment unit 220f can use one of the image evaluation values in the segment SG2 which is the non-empty section located on the back side of the organ from the empty section, for the empty section (segments SG3 and SG4) in which the representative evaluation value is not generated. FIG. 9 is a diagram illustrating an example of the adjustment of the evaluation result by the lesion evaluation adjustment unit 220f. Similar to FIG. 7, the result illustrated in FIG. 9 is a graph in which the horizontal axis represents the position from the segment SG5 to the segment SG1 and the vertical axis represents the representative evaluation value. In the drawing, there are a plurality of image evaluation values ("○") in the segment SG2.

As illustrated in FIG. 9, when there are a plurality of image evaluation values ("○") in the segment SG2, the estimated representative evaluation value of the segments SG3 and SG4 is not the representative evaluation value ("●") but is one of the image evaluation values of the segment SG2.

According to an embodiment, it is preferable that the lesion evaluation adjustment unit 220f defines the image evaluation value in the nearest section with the representative evaluation value closest to the empty section or the representative evaluation value in the nearest section as the estimated representative evaluation value, in the non-empty section located on the back side of the organ from the empty section. One of the image evaluation values in the nearest section or the representative evaluation value in the nearest section is nearest to the actual image evaluation value or the representative evaluation value in the empty section, and the difference is small, so the evaluation can be performed with high accuracy.

According to an embodiment, when the image or the image evaluation value is associated with the capture time or capture order information of the image, the lesion evaluation adjustment unit 220f preferably defines the image evaluation value corresponding to the image having the latest capture time or capture order among the images that are obtained by image-capturing the non-empty section located on the back side of the organ from the empty section, or the image evaluation value having the latest capture time or capture order as the estimated representative evaluation value among the image evaluation values of the image that is obtained by image-capturing the non-empty section located on the back side of the organ from the empty section. Originally, since if the empty section is evaluated, the image evaluation value that is closest to the capture time or capture order of the image used for the evaluation and corresponds to the capture time and capture order can be considered to be close to the image evaluation value or the representative evaluation value in the empty section, of the image evaluation value corresponding to the image with the latest capture time or capture order in which the non-empty section located on the back side of the organ is captured from the empty section or the image evaluation value of the image that is obtained by image-capturing the non-empty section located on the back side of the organ from the empty section, it is preferable to set the image evaluation value with the latest capture time or capture order as the estimated representative evaluation value in order to perform highly accurate evaluation.

Figure 10:
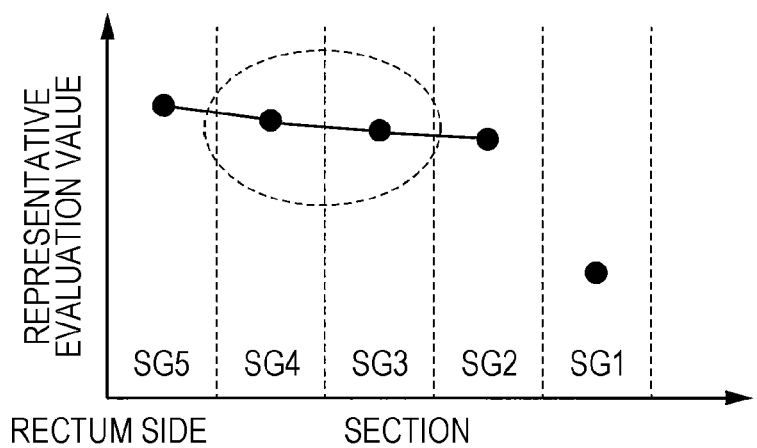
FIG. 10 is a diagram illustrating an example of the adjustment of the evaluation result by the lesion evaluation adjustment unit of the embodiment.

FIG. 10 is a diagram illustrating an example of the adjustment of the evaluation result by the lesion evaluation adjustment unit 220f. Similar to FIG. 7, the result illustrated in FIG. 10 is a graph in which the horizontal axis represents the position from the segment SG5 to the segment SG1 and the vertical axis represents the representative evaluation value.

As illustrated in FIG. 10, for the segments SG3 and SG4 that are the empty sections, the lesion evaluation adjustment unit 220f sets two of the representative evaluation values in each of the non-empty sections which has the empty section sandwiched between both sides thereof among the plurality of sections as the reference evaluation values, obtains the composite representative value obtained based on the reference evaluation value as the estimated representative evaluation value indicating the extent of the lesion, and assigns the estimated representative evaluation value to the empty section. When the representative evaluation value changes slightly between the segments SG2 and SG5, it is preferable to obtain the estimated representative evaluation value using, as the reference evaluation value, two of the representative evaluation value in each non-empty section which has the segments SG3 and SG4, which are the empty sections, sandwiched between both sides thereof for highly accurate evaluation. The lesion evaluation adjustment unit 220f obtains a composite representative value by interpolation using a straight line using, for example, two reference evaluation values.

The lesion evaluation adjustment unit 220f may define, as the estimated representative evaluation value, a weighted average value obtained by weighting and averaging the two reference evaluation values using a first weighting coefficient based on total length information of the length information of one of the non-empty sections on both the sides of the empty section and length information of the empty section and a second weighting coefficient based on total length information of length information of the other of the non-empty sections on both the sides and the length information of the empty section, but is preferable for highly accurate evaluation in the segments SG2 to SG5 in which the segment length is not constant. As the information on the lengths of the empty section and the non-empty section, the known lengths are used. For example, when the representative evaluation value in the segment SG2 is set as A2 and the representative evaluation value in the segment SG5 is set as A3, if a first weighting coefficient B5 is based on the total length information of the length information of the segments SG4 to SG5 and the length information of the segment SG3 and a second weighting coefficient B2 is based on the total length information of the length information of the segment SG2 and the length information of the segment SG3 (B2+B5=1), the estimated representative evaluation value in the segment SG3 can be expressed as $B5 \cdot A2 + B2 \cdot A5$.

Figure 11:
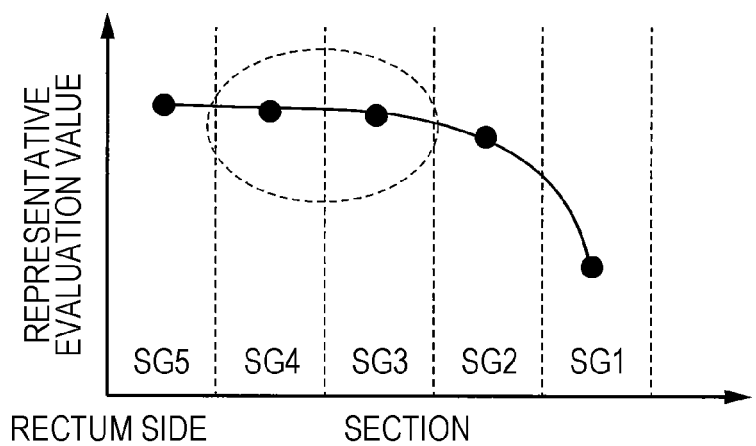
FIG. 11 is a diagram illustrating an example of the adjustment of the evaluation result by the lesion evaluation adjustment unit of the embodiment.

FIG. 11 is a diagram illustrating an example of the adjustment of the evaluation result by the lesion evaluation adjustment unit 220f. Similar to FIG. 7, the result illustrated in FIG. 11 is a graph in which the horizontal axis represents the position from the segment SG5 to the segment SG1 and the vertical axis represents the representative evaluation value.

As illustrated in FIG. 11, for the empty section, the lesion evaluation adjustment unit 220f obtains the estimated representative evaluation value indicating the extent of the lesion based on the representative evaluation values in the non-empty sections which have the empty section sandwiched between both sides thereof and assigns the estimated representative evaluation value to the empty section. In this case, the lesion evaluation adjustment unit 220f calculates the estimated representative evaluation value in the empty section by the interpolation by the curve fitting using the length information of each of the non-empty sections on both sides, the length information of the empty section, and the representative evaluation values in the non-empty section. As the expression used for the interpolation, the predetermined expression is used, for example, a B-spline function or a function of a cubic polynomial is used. In this way, the estimated representative evaluation value is calculated using the length information of the segments SG1 to SG5 and the representative evaluation value in the non-empty section, so a highly accurate evaluation can be obtained. As the information on the lengths of the empty section and the non-empty section, the known lengths are used.

The evaluation result integration unit 220g is configured to generate an evaluation result screen that shows the representative evaluation value and the estimated representative evaluation value corresponding to the sections. In this case, in the evaluation result screen, the estimated representative evaluation value is preferably represented in a display form that can be distinguished from the representative evaluation value. For example, when the estimated representative evaluation value and the representative evaluation value are indicated by numbers, the estimated representative evaluation value and the representative evaluation value are displayed in different colors, and when the estimated representative evaluation value and the representative evaluation value are displayed in a graph as illustrated in FIGS. 8 to 11, the color of the plot point of the estimated representative evaluation value may be different from the color of the plot point of the representative evaluation value, or the shape of the plot point of the estimated representative evaluation value may be different from the shape of the plot point of the representative evaluation value, and a background color of the region of the segment of the empty section may be different from the background color of the region of the segment of the non-empty section.

Note that the evaluation representative evaluation value in the empty section may be set by manual input by the subjective assessment of the surgeon or the operator who looks at the image displayed on the monitor 300. In this case, the manual input is performed using the operation panel 208 or a user interface such as a mouse or keyboard (not illustrated).

The evaluation unit 225 in the above-described embodiment is provided in the processor 200 for an electronic endoscope, but the evaluation unit 225 may not be provided in the processor 200 for an electronic endoscope. The distal end of the electronic scope 100 is inserted into the organ to store the plurality of images of biological tissue inside the organ in the memory, and it may be the data processing device configured to play back this stored image and evaluate the extent of lesion of the biological tissue. In this case, the data processing device includes at least the image evaluation value calculation unit 220b, the image-captured position information processing unit 220c, the lesion evaluation unit 220d, and the lesion evaluation adjustment unit 220f illustrated in FIG. 2. In this case, it is preferable to include the preprocessing unit 220a, the lesion part position calculation unit 220e, and the evaluation result integration unit 220g. The data processing device is configured by, for example, a computer.

As described above, according to the electronic endoscope system and the data processing device, the information on the image-captured position inside the organ that is obtained by capturing each image is used to calculate the representative evaluation values of the image evaluation values from the image evaluation values for each of the plurality of sections obtained by dividing the region inside the captured organ, but even for the empty section without the representative evaluation values, since the estimated representative evaluation value defined by the above method is assigned to the empty section, even if the examination is performed again at a later date in addition to being able to evaluate the spread of the depth direction of the organ in the biological tissue, it is possible to evaluate the degree of progression or retreat of the lesion.

Hereinabove, although the electronic endoscope system and the data processing device of the present invention have been described in detail, the electronic endoscope system and the data processing device of the present invention are not limited to the above embodiments, and various improvements and changes may be made without departing from the gist of the present invention.

REFERENCE SIGNS LIST

1 Electronic endoscope system
100 Electronic scope
102 LCB (Light Carrying Bundle)
104 Light distribution lens
106 Objective lens
108 Image sensor
108a IR (Infrared) cut filter
108b Bayer array color filter
112 Driver signal processing circuit
114 Memory
200 Processor
202 System controller
204 Memory
206 Timing controller
208 Operation panel
210 NIC(Network Interface Card)
220 Image processing unit
220a Preprocessing unit
220b Image evaluation value calculation unit
220c image-captured position information processing unit
220d Lesion evaluation unit
220e Lesion part position calculation unit
220f Lesion evaluation adjustment unit
220g Evaluation result integration unit
230 Light source unit
250 Position measurement system
300 Monitor
400 Printer
500 Network
600 Server

The invention claimed is:

1. An electronic endoscope system that evaluates an extent of a lesion in biological tissue in an organ from an image of the biological tissue that an electronic endoscope inserted into the organ captures, the electronic endoscope system comprising:
  an electronic endoscope configured to capture images of the biological tissue in the organ,
  a processor configured to include an evaluation unit configured to process a plurality of captured images of the biological tissue to evaluate the extent of the lesion in the organ; and
  a monitor configured to display an evaluation result of the extent of the lesion on a screen,
  wherein the evaluation unit includes:
  an image evaluation value calculation unit configured to calculate an image evaluation value indicating the extent of the lesion in an image of interest for at least some of a plurality of images of interest of a plurality of images that are obtained by image-capturing different locations of the biological tissue in the organ;
  an image-captured position information processing unit configured to associate the information on the image-captured position in the organ image-captured by the electronic endoscope with each of the images of interest;
  a lesion evaluation unit configured to sort each of the calculated image evaluation values to one of a plurality of sections obtained by dividing the region inside the organ by using the information on the image-captured position, perform processing to generate a representative evaluation values for each section from the sorted image evaluation value, and evaluate the spread of the lesion continuously spreading in the depth direction of the organ using the representative evaluation value;
  a lesion evaluation adjustment unit configured to assign one of the image evaluation values in a non-empty section which is located on a back side of the organ from an empty section and has the representative evaluation value generated therein among the plurality of sections, or a representative evaluation value obtained based on the image evaluation value in the non-empty section to the empty section as an estimated representative evaluation value in the empty section, for the empty section in which the representative evaluation value is not generated by the processing of the lesion evaluation unit among the plurality of sections; and an evaluation result integration unit configured to generate an evaluation result screen displaying the representative evaluation value and the estimated representative evaluation value corresponding to the section, wherein in the evaluation result screen, the estimated representative evaluation value is represented in a display form that can be distinguished from the representative evaluation value.

2. The electronic endoscope system according to claim 1, wherein the lesion evaluation adjustment unit defines one of the image evaluation values in a section nearest to the empty section or the representative evaluation value in the nearest section as the estimated representative evaluation value, in the non-empty section on the back side of the organ from the empty section.

3. The electronic endoscope system according to claim 1, wherein the image or the image evaluation value is associated with information on a capture time or a capture order of the image, and the lesion evaluation adjustment unit defines an image evaluation value corresponding to an image at which the capture time or the capture order is the latest among the images that are obtained by image-capturing the non-empty section on the back side of the organ from the empty section or the image evaluation value of the image at which the capture time or the capture order is the latest among the image evaluation values of the images that are obtained by image-capturing the non-empty section on the back side of the organ from the empty section, as the estimated representative evaluation value.

4. An electronic endoscope system that evaluates an extent of a lesion in biological tissue in an organ from an image of the biological tissue that an electronic endoscope inserted into the organ captures, the electronic endoscope system comprising:

an electronic endoscope configured to capture images of the biological tissue in the organ, a processor including an evaluation unit configured to process a plurality of captured images of the biological tissue to evaluate the extent of the lesion in the organ; and a monitor configured to display an evaluation result of the extent of the lesion on a screen, wherein the evaluation unit includes:

an image evaluation value calculation unit configured to calculate an image evaluation value indicating the extent of the lesion in an image of interest for at least some of a plurality of images of interest of a plurality of images that are obtained by image-capturing different locations of the biological tissue in the organ;

an image-captured position information processing unit configured to associate the information on the image-captured position in the organ image-captured by the electronic endoscope with each of the images of interest;

a lesion evaluation unit configured to sort each of the calculated image evaluation values to one of a plurality of sections obtained by dividing the region inside the organ by using the information on the image-captured position, perform processing to generate representative evaluation values for each section from the sorted image evaluation value, and evaluate the spread of the lesion continuously spreading in the depth direction of the organ using the representative evaluation value; and a lesion evaluation adjustment unit configured to set two of the representative evaluation values in each non-empty section which has an empty section sandwiched between both sides thereof among the plurality of sections and has the representative evaluation value generated therein as a reference evaluation value, and assign a composite evaluation value calculated based on the reference evaluation value to the empty section as an estimated representative evaluation value in the empty section, for the empty section in which the representative evaluation values are not generated by the processing of the lesion evaluation unit among the plurality of sections.

5. The electronic endoscope system according to claim 4, wherein the lesion evaluation adjustment unit defines, as the estimated representative evaluation value, a weighted average value obtained by weighting and averaging the two reference evaluation values using a first weighting coefficient based on total length information of length information of one of the non-empty sections on both the sides and length information of the empty section and a second weighting coefficient based on total length information of length information of the other of the non-empty sections on both the sides and the length information of the empty section.

6. An electronic endoscope system that evaluates an extent of a lesion in biological tissue in an organ from an image of the biological tissue that an electronic endoscope inserted into the organ captures, the electronic endoscope system comprising:

an electronic endoscope configured to capture images of the biological tissue in the organ, a processor including an evaluation unit configured to process a plurality of captured images of the biological tissue to evaluate the extent of the lesion in the organ; and a monitor configured to display an evaluation result of the extent of the lesion on a screen, wherein the evaluation unit includes:

an image evaluation value calculation unit configured to calculate an image evaluation value indicating the extent of the lesion in an image of interest for at least some of a plurality of images of interest of a plurality of images obtained by image-capturing different locations of the biological tissue in the organ;

an image-captured position information processing unit configured to associate the information on the image-captured position in the organ image-captured by the electronic endoscope with each of the images of interest;

a lesion evaluation unit configured to sort each of the calculated image evaluation values to one of a plurality of sections obtained by dividing the region inside the organ is divided by using the information on the image-captured position, perform processing to generate a representative evaluation values for each section from the sorted image evaluation value, and evaluate the spread of the lesion continuously spreading in the depth direction of the organ using the representative evaluation value; and a lesion evaluation adjustment unit configured to assign a composite representative evaluation value obtained based on the representative evaluation values in each non-empty section which has an empty section sandwiched between both sides thereof and has the representative evaluation values generated therein among the plurality of sections, for the empty section in which the representative evaluation values are not generated by the processing of the lesion evaluation unit among the plurality of sections to the empty section as an estimated representative evaluation value indicating the extent of the lesion in the empty section, and the lesion evaluation adjustment unit calculates the estimated representative evaluation value in the empty section by interpolation by curve fitting using length information of each of the non-empty sections on both sides, length information of the empty section, and the representative evaluation values in the non-empty section.

7. The electronic endoscope system according to claim 1, further comprising: a lesion part position calculation unit configured to set, as a start position or an end position of a lesion part, a position where the image evaluation value of the image of interest crosses a preset threshold value with the movement of the image-captured position of the image of interest and specify the start position or the end position in the organ from the information on the image-captured position of the image of interest, and wherein the lesion evaluation unit calculates the length in the depth direction of the lesion part from a specific result of the lesion part position calculation unit.

* * * * *